US012083083B2

(12) United States Patent
Pedersen et al.

(10) Patent No.: US 12,083,083 B2
(45) Date of Patent: *Sep. 10, 2024

(54) ANTIVIRAL COMPOSITIONS AND METHODS FOR INACTIVATING NON-ENVELOPED VIRUSES USING ALKYL 2-HYDROXYCARBOXYLIC ACIDS

(71) Applicant: ECOLAB USA INC., Saint Paul, MN (US)

(72) Inventors: Daniel E. Pedersen, Saint Paul, MN (US); Hilina Emiru, Saint Paul, MN (US); Carter M. Silvernail, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/653,611

(22) Filed: Mar. 4, 2022

(65) Prior Publication Data

US 2022/0184010 A1 Jun. 16, 2022

Related U.S. Application Data

(63) Continuation of application No. 16/946,744, filed on Jul. 2, 2020, now Pat. No. 11,298,329, which is a continuation of application No. 15/720,636, filed on Sep. 29, 2017, now Pat. No. 10,736,860, which is a continuation of application No. 13/795,219, filed on Mar. 12, 2013, now Pat. No. 9,808,435.

(51) Int. Cl.
*A61K 31/19* (2006.01)
*A01N 25/30* (2006.01)
*A01N 31/02* (2006.01)
*A01N 37/36* (2006.01)
*A01N 41/02* (2006.01)
*A01N 41/04* (2006.01)
*A61K 31/045* (2006.01)
*A61K 31/20* (2006.01)

(52) U.S. Cl.
CPC .............. *A61K 31/19* (2013.01); *A01N 25/30* (2013.01); *A01N 31/02* (2013.01); *A01N 37/36* (2013.01); *A01N 41/02* (2013.01); *A01N 41/04* (2013.01); *A61K 31/045* (2013.01); *A61K 31/20* (2013.01)

(58) Field of Classification Search
CPC ......... A01N 37/00; A01N 31/02; A01N 37/36
See application file for complete search history.

(56) References Cited

U.S. PATENT DOCUMENTS

| 4,076,917 A | 2/1978 | Swift et al. |
|---|---|---|
| 4,208,293 A | 6/1980 | Zaweski |
| 4,325,973 A | 4/1982 | Graham et al. |
| 4,729,769 A | 3/1988 | Schlicht et al. |
| 4,975,217 A * | 12/1990 | Brown-Skrobot ..... A61K 31/19 514/711 |
| 4,981,845 A * | 1/1991 | Pereira ................... A61Q 17/04 514/657 |
| 5,443,817 A | 8/1995 | Zimmerman et al. |
| 6,184,190 B1 | 2/2001 | D'Ambrogio et al. |
| 6,238,682 B1 | 5/2001 | Klofta et al. |
| 6,410,597 B1 | 6/2002 | Bieberich et al. |
| 7,569,530 B1 | 8/2009 | Pan et al. |
| 7,592,300 B2 | 9/2009 | Taylor et al. |
| 9,808,435 B2 * | 11/2017 | Pedersen ................. A01N 31/02 |
| 10,736,860 B2 * | 8/2020 | Pedersen ............... A61K 31/045 |
| 11,298,329 B2 * | 4/2022 | Pedersen ................. A01N 41/02 |
| 2003/0219600 A1 | 11/2003 | Mitchell et al. |
| 2003/0235550 A1 | 12/2003 | Pan et al. |
| 2005/0113276 A1 | 5/2005 | Taylor et al. |
| 2006/0293201 A1 | 12/2006 | Simon et al. |
| 2006/0293214 A1 * | 12/2006 | Cheng .................. C11D 3/2006 510/504 |
| 2007/0184013 A1 | 8/2007 | Snyder et al. |
| 2007/0185216 A1 | 8/2007 | Snyder et al. |
| 2007/0274940 A1 | 11/2007 | Fuls et al. |
| 2007/0275929 A1 | 11/2007 | Fuls et al. |
| 2008/0095814 A1 | 4/2008 | Taylor et al. |
| 2008/0267904 A1 | 10/2008 | Taylor et al. |
| 2008/0286223 A1 | 11/2008 | Fuls et al. |
| 2009/0035339 A1 | 2/2009 | Istvan et al. |
| 2009/0312226 A1 | 12/2009 | Szewczyk et al. |
| 2010/0240600 A1 * | 9/2010 | Shimamoto ............ A61K 9/06 514/23 |

(Continued)

FOREIGN PATENT DOCUMENTS

| EP | 0403304 A2 | 12/1990 |
|---|---|---|
| EP | 0588912 | 4/2003 |

(Continued)

OTHER PUBLICATIONS

Dowfax product page (published 2000) (Year: 2000).*
Dowfax Product Page, published 2000.
Harper, D. R. et al. "Antiviral activity of 2-hydroxy fatty acids", Chemistry & Chemotherapy (1996) 7 (3) 138-141. 1996.
Ecolab USA Inc., PCT/US2014/019951 filed Mar. 3, 2014, "Notification of Transmittal of The International Search Report and The Written Opinion of The International Searching Authority, or The Declaration" mailed Jun. 9, 2014.

*Primary Examiner* — Theodore R. Howell
*Assistant Examiner* — George W Kosturko
(74) *Attorney, Agent, or Firm* — McKee, Voorhees & Sease, PLC

(57) ABSTRACT

The present invention is directed to antiviral compositions that provide efficacy against non-envelope viruses such as noroviruses. The antiviral compositions comprise an alkyl 2-hydroxycarboxylic acid and an effective amount of a sulfonated surfactant. The composition may be used as a topical on human skin, as a hand sanitizer or as a hard surface cleaning composition.

16 Claims, No Drawings

(56) References Cited

U.S. PATENT DOCUMENTS

| | | |
|---|---|---|
| 2010/0246060 A1 | 9/2010 | Sasaki |
| 2011/0207649 A1 | 8/2011 | Molinaro et al. |
| 2012/0071438 A1 | 3/2012 | Pedersen et al. |

FOREIGN PATENT DOCUMENTS

| | | | |
|---|---|---|---|
| EP | 2153838 | 2/2010 | |
| GB | 760620 | 11/1956 | |
| WO | 2004108091 | 12/2004 | |
| WO | WO-2006138008 A2 * | 12/2006 | ........... H03K 17/955 |
| WO | WO-2006138088 A2 * | 12/2006 | ............. A01N 37/10 |
| WO | WO-2007001594 A2 * | 1/2007 | ............. A01N 37/36 |
| WO | 2007095008 A2 | 8/2007 | |
| WO | 2008021441 | 2/2008 | |
| WO | 2012121179 A1 | 9/2012 | |

* cited by examiner

ANTIVIRAL COMPOSITIONS AND METHODS FOR INACTIVATING NON-ENVELOPED VIRUSES USING ALKYL 2-HYDROXYCARBOXYLIC ACIDS

CROSS-REFERENCE TO RELATED APPLICATIONS

This application is a continuation application of U.S. Ser. No. 16/946,744, filed Jul. 2, 2020, which is a continuation of U.S. Ser. No. 15/720,636, filed Sep. 29, 2017, now U.S. Pat. No. 10,736,860, issued Aug. 11, 2020, which is a continuation of claims priority to application U.S. Ser. No. 13/795,219 filed Mar. 12, 2013, now U.S. Pat. No. 9,808,435, issued Nov. 7, 2017, all of which are incorporated herein by reference in their entireties.

FIELD OF THE INVENTION

The present invention relates to antiviral compositions having efficacy against non-enveloped viruses such as norovirus. More particularly, the present invention relates to antiviral compositions for use in topical skin applications, hand sanitizer compositions, hard surface cleaners and the like, comprising alkyl 2-hydroxycarboxylic acids. The compositions are effective at inactivating and reducing viral populations of non-enveloped viruses by greater than 3 logs.

BACKGROUND OF THE INVENTION

Pathogenic viruses can be classified into two general types with respect to the viral structure: enveloped viruses and non-enveloped viruses. Some well-known enveloped viruses include herpes virus, influenza virus; paramyxovirus, respiratory syncytial virus, corona virus, HIV, hepatitis B virus, hepatitis C virus and SARS-CoV virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus.

It is known in the art that "enveloped" viruses are relatively sensitive and, thus, can be inactivated by commonly used disinfectants. In contrast, non-enveloped viruses are substantially more resistant to conventional disinfectants and are significantly more environmentally stable than enveloped viruses. Although a number of non-enveloped viruses can be inactivated with relatively high concentrations of formaldehyde, the use of formaldehyde is undesirable because of its toxicity.

The non-enveloped virus Norovirus (NoV), also known previously as "Norwalk-Like Virus" (NLV) or small round structured virus, is the most important viral pathogen of epidemic acute gastroenteritis that occurs in both developed and developing countries. NoV belongs to the Caliciviridae family and are icosahedral, single stranded, positive-sense RNA viruses whose capsids are composed of 180 copies of a single major structural protein. Noroviruses are estimated to cause 23 million cases of acute gastroenteritis in the United States per year, and are the leading cause of gastroenteritis in the United States. Of viruses, only the common cold is reported more often than viral gastroenteritis (norovirus). Norovirus causes nausea, vomiting (sometimes accompanied by diarrhea), and stomach cramps. This infection typically is spread from person to person by direct contact.

Noroviruses are very highly contagious and can spread easily from person to person. People can become infected with the norovirus in several ways, including, eating food or drinking liquids that are contaminated with norovirus; touching surfaces or objects contaminated with norovirus, and then placing their hands in their mouths; or having direct contact with another person who is infected and showing symptoms (for example, when caring for someone who is ill, or sharing foods or eating utensils with someone who is ill). During outbreaks of norovirus gastroenteritis, several modes of transmission have been documented, for example, initial foodborne transmission in a restaurant, followed by secondary person-to-person transmission to household contacts. No evidence suggests that norovirus infection occurs through the respiratory system.

Protracted outbreaks of norovirus disease have been reported among elderly persons living in institutional settings, e.g., nursing homes. In some cases, the outbreak was initially caused by exposure to a fecally-contaminated vehicle (e.g., food or water). Then, the outbreak spreads through person-to-person transmission among the residents. This spread is facilitated by the enclosed living quarters and reduced levels of personal hygiene that result from incontinence, immobility, or reduced mental alertness. Because of underlying medical conditions, the disease among these elderly persons can be severe or fatal.

Passengers and crew members on cruise ships and naval vessels are frequently affected by outbreaks of gastroenteritis. Cruise ships often dock in countries where sanitation levels are inadequate, thus increasing the contamination risk of water and food taken aboard or having a passenger board with an active infection. After a passenger or crew member brings the norovirus on board, the close living quarters on ships amplify opportunities for person-to-person transmission. Furthermore, the arrival of new and susceptible passengers every few days or weeks on affected cruise ships provides an opportunity for sustained transmission during successive cruises. Norovirus outbreaks extending beyond twelve successive cruises have been reported.

Currently, no antiviral medication against norovirus is available, and no standard method to prevent infection exists. Norovirus infection cannot be treated with antibiotics. Noroviruses also are relatively resistant to environmental challenge. Noroviruses can survive freezing, temperatures as high as 60° C., and even have been associated with illness after being steamed in shellfish. Moreover, noroviruses can survive in up to 10 ppm chlorine, which is well in excess of chlorine levels routinely present in public water systems. Accordingly it is an object herein to provide a composition for inactivation of non-enveloped viruses that is may be used topically on skin and can also function as a hard surface cleaner.

It is yet another object of the invention to provide a composition and method for viral inactivation of non-enveloped viruses that results in a greater than 3 log reduction of a population.

Other objects, aspects and advantages of this invention will be apparent to one skilled in the art in view of the following disclosure, the drawings, and the appended claims.

SUMMARY OF THE INVENTION

The present invention is directed to antiviral compositions that provide rapid antimicrobial effectiveness against noroviruses. The compositions provide a substantial reduction in norovirus population, up to 3 logs in less than about one minute.

More particularly, the present invention relates to antimicrobial compositions comprising a C1-C6 linear and/or branched alcohol, one or more alkyl 2-hydroxycarboxylic acids and a sulfonated surfactant. The composition may be used as a topical on human skin, as a hand sanitizer or as a hard surface cleaning composition.

Another aspect of the present invention is to provide a liquid, antimicrobial composition comprising:
(a) about 30% to about 99%, by weight, of a linear or branched alcohol, such as a $C_{1-6}$ alcohol;
(b) a viricidally effective amount of an alkyl 2-hydroxycarboxylic acid with the following structure:

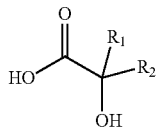

Wherein $R_1$ and $R_2$ are the same or different and independently selected from an alkyl group of saturated or unsaturated, substituted or unsubstituted, isomeric or non-isomeric, straight or branched chain, having 6 to 30 carbon atoms
(c) an effective amount of a sulfonated surfactant, and
(d) water;
wherein the composition has a pH of about 2.5 to about 6.8 for topical formulations, and 1.5 to about 6.8 for a hard surface cleaning formulation. Additional functional components and excipients may also be present.

In a preferred embodiment the alkyl 2-hydroxycarboxylic acid is present in an amount of from about 0.5% to about 10% by weight of the composition. The sulfonated surfactant is present, is may be present in an amount of from about 0.25% to about 10% by weight of the composition.

Another aspect of the present invention is to provide an antimicrobial composition having antibacterial and antiviral activity comprising a linear or branched C1 to C6 alcohol; one or more alkyl 2-hydroxycarboxylic acids and a sulfonated surfactant.

Yet another aspect of the present invention is to provide a composition and method of interrupting transmission of a norovirus from animate and inanimate surfaces to an animate surface, especially human skin and mouth. Especially provided is a method and composition for controlling the transmission of norovirus by effectively controlling noroviruses present on human skin and continuing to control noroviruses for a period of about four or more hours, and up to about eight hours, after application of the composition to the skin.

The antimicrobial compositions of the present invention are highly efficacious in household cleaning applications (e.g., hard surfaces, like floors, countertops, tubs, dishes, and softer cloth materials, like clothing), personal care applications (e.g., lotions, shower gels, soaps, shampoos, and wipes), and industrial and hospital applications (e.g., sterilization of instruments, medical devices, and gloves). The present compositions efficaciously and rapidly clean and disinfect surfaces that are infected or contaminated with Gram negative bacteria, Gram positive bacteria, and particularly non-enveloped viruses such as noroviruses (e.g., rhinoviruses). The present compositions also provide a persistent antiviral effectiveness.

Another aspect of the present invention is to provide consumer products based on an antimicrobial composition of the present invention, for example, a skin cleanser, a body splash, a surgical scrub, a wound care agent, a hand sanitizer gel, a disinfectant, a pet shampoo, a hard surface sanitizer, a lotion, an ointment, a cream, a swab, a wipe, and the like. A composition of the present invention can be a rinse-off product, but preferably is a leave-on product. The compositions are esthetically pleasing and nonirritating to the skin.

These and other novel aspects and advantages of the present invention are set forth in the following, nonlimiting detailed description of the preferred embodiments

DETAILED DESCRIPTION

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

"Cleaning" means to perform or aid in soil removal, bleaching, microbial population reduction, rinsing, or combination thereof.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "weight percent," "wt. %," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt. %," etc.

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The term "alkyl" or "alkyl groups," as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "aromatic" as used herein, refers to a hydrocarbon with alternating double and single bonds between carbon atoms forming rings. The configuration of six carbon atoms in aromatic compounds is known as a benzene ring, after the simplest possible such hydrocarbon, benzene. Aromatic hydrocarbons can be monocyclic (MAH) or polycyclic (PAH). In one embodiment, "aromatic" is a 6-12 membered monocyclic or bicyclic system. Aromatics include, but are not limited to, benzyl, phenyl, naphthalenyl, fluorenyl, indenyl, azulenyl, and anthracenyl.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bactericidal and the later, bacteriostatic. A sanitizer and a disinfectant are, by definition, agents which provide antibacterial or bactericidal activity. In contrast, a preservative is generally described as an inhibitor or bacteriostatic composition.

For the purpose of this patent application, successful reduction of microorganisms is achieved when the populations of microorganisms are reduced by about 50%, by significantly more than is achieved by a wash with water, or at least about 0.3-1 log.sub. 10: Larger reductions in microbial population provide greater levels of protection. In this application, such a population reduction is the minimum acceptable for the processes. Any increased reduction in population of microorganisms is an added benefit that provides higher levels of protection.

The term "disinfectant," as used herein, refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15.sup.th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The phrase "food processing surface" or, "food surface," as used herein, refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food antispoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

The phrase "health care surface," as used herein, refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or woven and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

The term "instrument," as used herein, refers to the various medical or dental instruments or devices that can benefit from cleaning with a reduced-odor composition according to the present invention. The phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

The terms "agricultural" or "veterinary" objects or surfaces, as used herein, include animal feeds, animal watering stations and enclosures, animal quarters, animal veterinarian clinics (e.g. surgical or treatment areas), animal surgical areas, and the like.

The term "microorganisms," as used herein, refers to any noncellular or unicellular (including colonial) organism. Microorganisms include all prokaryotes. Microorganisms include bacteria (including cyanobacteria), lichens, microfungi, protozoa, virinos, viroids, viruses, (enveloped and non-enveloped) and some algae. As used herein, the term "microbe" is synonymous with microorganism.

The term "object", as used herein, refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

The term "sanitizer," as used herein, refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25° C.+/−2° C., against several test organisms.

The term "ware," as used herein, refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compositions of the invention include polyethylene terephthalate (PET).

The recitation of numerical ranges by endpoints includes all numbers subsumed within that range (e.g., 1 to 5 includes 1, 1.5, 2, 2.75, 3, 3.80, 4, and 5).

The terms "include" and "including" when used in reference to a list of materials refer to but are not limited to the materials so listed.

Compositions of the Invention

The present invention relates to antimicrobial compositions comprising a C1-C6 linear and/or branched alcohol, one or more alkyl 2-hydroxycarboxylic acid and a sulfonated surfactant. The compositions provide rapid antiviral effectiveness, including most notably, effectiveness against non-enveloped viruses such as noroviruses. The compositions provide a substantial reduction in norovirus population, up to 3 logs in less than about one minute.

Accordingly, one aspect of the present invention is to provide an antiviral composition that is highly effective at inactivating or destroying viruses harmful to human health, particularly noroviruses.

Another aspect of the present invention is to provide a liquid, antimicrobial composition comprising:
  (a) about 30% to about 99%, by weight, of a linear and or branched C1 to C6 alcohol;
  (b) a viricidally effective amount of an alkyl 2-hydroxycarboxylic acid with the structure:

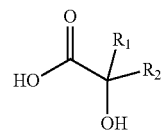

Wherein $R_1$ and $R_2$ are the same or different and independently selected from an alkyl group of saturated or unsaturated, substituted or unsubstituted, isomeric or non-isomeric, straight or branched chain, having 6 to 30 carbon atoms
  (c) an effective amount of a sulfonated surfactant, and
  (d) water;
wherein the composition has a pH of about 2.5 to about 6.8 for topical formulations, and 1.5 to about 6.8 for a hard surface cleaning formulation. Additional functional components and excipients may also be present. In a preferred embodiment the alkyl 2-hydroxycarboxylic acid is present in an amount of from about 0.5% to about 10% by weight of the composition. The sulfonated surfactant is present in an amount of from about 0.25% to about 10% by weight of the composition.

Another aspect of the present invention is to provide an antimicrobial composition having antibacterial and antiviral activity comprising a linear or branched C1 to C6 alcohol; one or more alkyl 2-hydroxycarboxylic acids and a sulfonated surfactant.

The following ingredients may be present in an antiviral compositions of the present invention.

2-Hydroxycarboxylic Acid

One aspect of the invention is a 2-hydroxycarboxylic acid. The 2-hydroxycarboxlylic acid comprises organic carboxylic acids in which at least one hydroxy group is attached to the 2 position carbon atom of the acid. The generic structure of such 2-hydroxycarboxylic acids may be represented as follows:

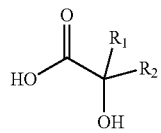

Where $R_1$ and $R_2$ may be the same or different and are independently selected from an alkylgroup of saturated or unsaturated, substituted or unsubstituted, isomeric or non-isomeric, straight or branched chain, having 6 to 30 carbon atoms, (preferably 6-20) and in addition $R_1$ and $R_2$ may carry OH, CHO, COOH and alkoxy group having 1 to 9 carbon atoms. 2-Hydroxycarboxylic acids may be present as a free acid or lactone form, or in a salt form with an organic base or an inorganic alkali. 2-Hydroxycarboxylic acids may exist as stereoisomers as D, L, and DL forms when $R_1$ and $R_2$ are not identical. Typical alkyl groups for $R_1$ and $R_2$ include methyl, ethyl, propyl, isopropyl, butyl, pentyl, octyl, decyl, dodecyl, tetradecyl, hexadecyl, benzyl, and phenyl, Examples of suitable 2-hydroxycarboxylic acids include, but are not limited to: 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxy-dodecanoic acid, 2-hydroxytetradecanoic acid, 2-hydroxyhexadecanoic acid, 2-hydroxyoctadecanoic acid, 2-hydroxyeicosanoic acid, 2-hydroxytetraeicosanoic acid (Cerebronic and Alpha hydroxynervonic acid), The alkyl groups may be a branched alklane. Examples of suitable branched alkanes may have, but are not limited to the following structure:

Wherein n=C1-C20 linear alkane; $R_3$=C1-C20 linear alkane and combinations thereof such that the total number of carbon atoms in the branched alkane is from about 6 to about 30.

The 2-hydroxycarboxylic acids may be present in forms other than the acid, such as, for example, salts or lactones. Typical lactone forms which may be used in accordance with this invention include, for example, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

In a preferred embodiment the 2-hydroxycarboxylic acid is an alkyl 2-hydroxycoarboxylic acid. In a more preferred embodiment the alkyl hydroxyl carboxylic acid is a C6 to C30 carboxylic acid.

Carrier

The carrier in the present composition comprises water and/or polyol. It should be appreciated that the water may be provided as deionized water or as softened water. The water provided as part of the concentrate can be relatively free of hardness. It is expected that the water can be deionized to remove a portion of the dissolved solids. That is, the concentrate can be formulated with water that includes dissolved solids, and can be formulated with water that can be characterized as hard water.

Anonic Sulfonated Surfactant

The composition includes an anionic sulfonated surfactant. The surfactant can be included in a composition in an amount of 0.25% to about 10%, and typically 0.25% to about 7.5%, by weight, of the composition. More typically, if present at all, the composition contains about 0.5% to about 5%, by weight of the surfactant. The optional surfactant is stable at the pH of the composition and is compatible with the other ingredients present in the composition.

The compositions, therefore, can contain an anionic surfactant having a hydrophobic moiety, such as a carbon chain including about 8 to about 30 carbon atoms, and particularly about 12 to about 20 carbon atoms, and further has a hydrophilic moiety, of sulfate or sulfonate, Often, the hydrophobic carbon chain is etherified, such as with ethylene oxide or propylene oxide, to impart a particular physical property, such as increased water solubility or reduced surface tension to the anionic surfactant.

Suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, sulfosuccinates, fatty acid amide polyoxyethylene sulfates, Specific, nonlimiting classes of anionic surfactants useful in the present invention include, but are not limited to, a $C_8$-$C_{18}$ alkyl sulfonate, a $C_8$-$C_{18}$ alkyl sulfate, a $C_8$-$C_{18}$ alkyl ether sulfate having one or two moles of ethoxylation, a $C_8$-$C_{18}$ sulfoacetate, a $C_8$-$C_{18}$ sulfosuccinate, a $C_8$-$C_{18}$ alkyl diphenyl oxide disulfonate, a $C_8$-$C_{18}$ alpha-olefin sulfonate, a methyl ester sulfonate, and mixtures thereof. The $C_8$-$C_{18}$ alkyl group contains eight to eighteen carbon atoms, and can be straight chain (e.g., lauryl) or branched (e.g., 2-ethylhexyl). The cation of the anionic surfactant can be an alkali metal (preferably sodium or potassium), ammonium, $C_1$-$C_4$ alkylammonium (mono-, di-, tri-), or $C_1$-$C_3$ alkanolammonium (mono-, di-, tri-). Lithium and alkaline earth cations (e.g., magnesium) can be used, but are not preferred.

Specific surfactants include, but are not limited to, lauryl sulfates, octyl sulfates, 2-ethylhexyl sulfates, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, cetyl sulfates, and similar surfactants.

Compositions with a Linear or Branched C1 to C6 Alcohol

The compositions of the present invention exhibit enhanced efficacy against viruses, particularly, non-enveloped viruses, when compared to the efficacy of a linear or branched C1 to C6 alcohol alone. Whereas $C_{1-6}$ alcohols have little efficacy against non-enveloped virus, the efficacy may be enhanced by combining the $C_{1-6}$ alcohol with a combination of an effective amount of one or more alkyl 2-hydroxycarboxylic acids; and an effective amount of a sulfonated surfactant.

In one or more embodiments, the antiviral composition exhibits an increased efficacy against non-enveloped viruses when compared to a composition containing an equivalent amount of a branched and/or linear $C_{1-6}$ alcohol. In certain embodiments, a synergistic effect is seen. In other words, the efficacy of the antiviral composition against non-enveloped virus is greater than the sum of the efficacies of equivalent amounts of the individual components.

Therefore, the present invention can provide a virucidally-enhanced alcoholic composition comprising a polyol, alkyl 2-hydroxycarboxylic acid and a sulfonated surfactant. Examples of lower alkanols include, but are not limited to, methanol, ethanol, propanol, isopropanol, butanol, pentanol, hexanol, and isomers and mixtures thereof. In one embodiment, the alcohol comprises ethanol, propanol, or butanol, or isomers or mixtures thereof. In another embodiment, the alcohol comprises ethanol.

The antiviral composition comprises, if present, an amount of alcohol of at least about 30 percent by weight. In embodiments where rapid antimicrobial efficacy is not a requirement, the amount of alcohol may be reduced. In one embodiment, the composition comprises at least about 50 weight percent alcohol, in another embodiment, the composition comprises at least about 55 weight percent alcohol, in yet another embodiment, the composition comprises at least about 60 weight percent alcohol. More or less alcohol may be required in certain instances, depending particularly on other ingredients and/or the amounts thereof employed in the composition. In certain embodiments, the antiviral composition comprises from about 30 weight percent to about 99 weight percent alcohol, in other embodiments, the composition comprises from about 40 weight percent to about 95 weight percent of alcohol, in yet other embodiments, the composition comprises from about 50 weight percent to about 90 weight percent of alcohol, and in still other embodiments, the composition comprises from about 55 weight percent to about 85 weight percent of alcohol, based upon the total weight of the antiviral composition.

Additional Functional Materials

The antiviral composition can include additional components or agents, such as additional functional materials. The functional materials provide desired properties and functionalities to the antimicrobial composition. For the purpose of this application, the term "functional materials" include a material that when dispersed or dissolved in a use and/or concentrate solution, such as an aqueous solution, provides a beneficial property in a particular use. The antiviral composition may optionally contain other disinfectants, sanitizers, dyes, thickening or gelling agents, and perfumes. Some particular examples of functional materials are discussed in more detail below, but it should be understood by those of skill in the art and others that the particular materials discussed are given by way of example only, and that a broad variety of other functional materials may be used. For example, may of the functional material discussed below relate to materials used in disinfecting and/or cleaning applications, but it should be understood that other embodiments may include functional materials for use in other applications. Such additional functional materials or optional components typically are present, individually, from 0% to about 5%, by weight, of the composition, and, collectively, from 0% to about 20%, by weight of the composition.

Classes of optional ingredients include, but are not limited to, hydrotopes, dyes, fragrances, gelling agents, buffering agents, antioxidants, skin conditioners and protectants, chelating agents, opacifiers, vitamins, and similar classes of optional ingredients known to persons skilled in the art. Specific classes of optional ingredients include vitamins A, E, and C as vitamins; and EDTA compounds as chelating agents.

Skin Conditioners

The composition may include skin conditioners. Examples of optional skin conditioners include emollients, such as cetyl myristate, glyceryl dioleate, isopropyl myristate, lanolin, methyl laurate. PPG-9 laurate, octyl palmitate, and PPG-5 lanoate, for example. The skin conditioner also can be a humectant, for example, glucamine and pyridoxine glycol. Occlusive skin conditioners, for example, aluminum lanolate, corn oil, methicone, coconut oil, stearyl stearate, phenyl trimethicone, trimyristin, olive oil, and synthetic wax, also can be used. Combinations of the classes of skin conditioners, in addition to miscellaneous skin conditioners known to persons skilled in the art, alone or in combination can be used. Nonlimiting examples of miscellaneous skin conditioners also are disclosed in U.S. Pat. No. 6,136,771, incorporated herein by reference.

Antioxidant

The composition may optionally include an antioxidant for improved skin condition through the removal of free radicals, and improved product stability. Some non-limiting examples of antioxidants include ascorbic acid and ascorbic acid derivatives, BHA, BHT, betacarotene, cysteine, erythorbic acid, hydroquinone, tocopherol and tocopherol derivatives, and the like.

If an antioxidant is included, it is preferably present in the composition in an amount from about 0.001 to about 2 wt. %, from about 0.01 to about 1 wt. %, and from about 0.05 to about 0.5 wt. %.

Fragrance

The composition may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (Ocimum basilicum) oil, bay (Pimento acris) oil, bee balm (Monarda didyma) oil, bergamot (Citrus aurantium bergamia) oil, cardamom (Elettaria cardamomum) oil, cedarwood (Cedrus atlantica) oil, chamomile (Anthemis nobilis) oil, cinnamon (Cinnamomum cassia) oil, citronella (Cymbopogon nardus) oil, clary (Salvia sclarea) oil, clove (Eugenia caryophyllus) oil, cloveleaf (Eufenia caryophyllus) oil, Cyperus esculentus oil, cypress (Cupressus sempervirens) oil, Eucalyptus citriodora oil, geranium maculatum oil, ginger (Zingiber officinale) oil, grapefruit (Citrus grandis) oil, hazel (Corylus avellana) nut oil, jasmine (Jasminum officinale) oil, Juniperus communis oil, Juniperus oxycedrus tar, Juniperus virginiana oil, kiwi (Actinidia chinensis) water, lavandin (Lavandula hybrida) oil, lavender (Lavandula angustifolia) oil, lavender (Lavandula angustifolia) water, lemon (Citrus medica limonum) oil, lemongrass (Cymbopogon schoenanthus) oil, lime (Citrus aurantifolia) oil, linden (Tilia cordata) oil, linden (Tilia cordata) water, mandarin orange (Citrus nobilis) oil, nutmeg (Myristica fragrans) oil, orange (Citrus aurantium dulcis) flower oil, orange (Citrus aurantium dulcis) oil, orange (Citrus aurantium dulcis) water, patchouli (Pogostemon cablin) oil, peppermint (Menthe piperita) oil, peppermint (Menthe peperita) water, rosemary (Rosmarinus officinalis) oil, rose oil, rose (Rosa damascena) extract, rose (Rosa multiflora) extract, rosewood (Aniba rosaeodora) extract, sage (Salvia officinalis) oil, sandalwood (Santalum album) oil, spearmint (Menthe viridis) oil, tea tree (Melaleuca alternifolia) oil, and ylang ylang (Cananga odorata) oil. Some non-limiting examples of synthetic hydrocarbon fragrances include caryophyllene, .beta.-farnesene, limonene, .alpha.-pinene, and .beta.-pinene. Some non-limiting examples of synthetic alcohol fragrances include Bacdanol, citronellol, linalool, phenethyl alcohol, and .alpha.-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, .alpha.-ionone, isocyclemone E, koavone, muscone, and tonalide. Some non-limiting examples of synethetic ester fragrances include benzyl acetate, 4-t-butylcyclohexyl acetate (cis and trans), cedryl acetate, cyclacet, isobornyl acetate, and .alpha.-terpinyl acetate (R=acetyl). Some non-limiting examples of synthetic lactone fragrances include coumarin, jasmine lactone, muskalactone, and peach aldehyde. Some non-limiting examples of synthetic ether fragrances include Ambroxan, Anther, and Galaxolide. Some non-limiting examples of synthetic nitrile fragrances include cinnamonitrile and gernonitrile. Finally, some non-limiting examples of synthetic polyfunctional fragrances include amyl salicylate, isoeugenol, Hedione, heliotropine, Lyral, and vanillin.

The composition may include a mixture of fragrances including a mixture of natural and synthetic fragrances. The fragrance can be present in a composition in an amount up to about 5 wt. %, preferably from about 0.01 to about 3 wt. %, from about 0.05 to about 1 wt. %, and from about 0.1 to about 0.2 wt. %.

Dye

The composition may optionally include a dye. Examples of dyes include any water soluble or product soluble dye, any FD&C or D&C approved dye, Blue 1, FD&C Yellow 5, Resorcin Brown, Red 40, Direct Blue 86 (Miles), Basic Violet 10 (Clariant), Acid Yellow 23 (GAF), Acid Yellow 17 (Sigma Chemical), Sap Green (Keyston Analine and Chemical), Metanil Yellow (Keyston Analine and Chemical), Acid Blue 9 (Hilton Davis), Sandolan Blue/Acid Blue 182 (Clariant), Hisol Fast Red (Capitol Color and Chemical), Fluorescein (Capitol Color and Chemical), Acid Green 25 (Ciba Specialties), and the like. The dye is preferably a water soluble dye. Also, the dye is preferably a FD&C or D&C approved dye.

The dye can be present in a use composition in an amount up to about 0.5 wt. %, preferably from about 0.00001 to about 0.1 wt. %, from about 0.0001 to about 0.01 wt. %, and from about 0.0001 to about 0.0005 wt. %.

pH-Adjusting Compound

The antimicrobial composition of the present invention does not rely upon a low pH or a high pH to provide a rapid reduction in microbial populations. Antimicrobial populations of the present invention have a pH of about 5.0 to about 12.0. Within this pH range, the present compositions effectively reduce microbial populations, and are consumer acceptable, i.e., are mild to the skin, are phase stable, and generate copious, stable foam. In some instances a pH adusting compound may be necessary in a sufficient amount to provide a desired composition pH. To achieve the full advantage of the present invention, the pH-adjusting compound is present in an amount of about 1.5% to about 3.5%, by weight.

Examples of basic pH-adjusting compounds include, but are not limited to, ammonia; mono-, di-, and trialkyl amines; mono-, di-, and trialkanolamines; alkali metal and alkaline earth metal hydroxides; alkali metal phosphates; alkali sulfates; alkali metal carbonates; and mixtures thereof. However, the identity of the basic pH adjuster is not limited, and any basic pH-adjusting compound known in the art can be used. Specific, nonlimiting examples of basic pH-adjusting compounds are ammonia; sodium, potassium, and lithium hydroxide; sodium and potassium phosphates, including hydrogen and dihydrogen phosphates; sodium and potassium carbonate and bicarbonate; sodium and potassium sulfate and bisulfate; monoethanolamine; trimethylamine; isopropanolamine; diethanolamine; and triethanolamine.

The identity of an acidic pH-adjusting compound is not limited and any acidic pH-adjusting compound known in the art, alone or in combination, can be used. Examples of specific acidic pH-adjusting compounds are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid.

Surfactants

The methods and compositions of the invention can also include further surfactants in addition to the optional anionic sulfonated surfactant. Surfactants include water soluble or water dispersible nonionic, semi-polar nonionic (supra), anionic (other than sulfonated), cationic, amphoteric, or zwitterionic surface-active agents; viscoelastic surfactants or any combination thereof. A typical listing of the classes and species of surfactants useful herein appears in U.S. Pat. No. 3,664,961 issued May 23, 1972, to Norris.

Nonionic Surfactants

Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants in the present invention include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronico manufactured by BASF Corp.

Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from 1,000 to 4,000. Ethylene oxide is then added to sandwich this hydrophobe between hydrophilic groups, controlled by length to constitute from about 10% by weight to about 80% by weight of the final molecule.

Tetronic® compounds are tetra-functional block copolymers derived from the sequential addition of propylene oxide and ethylene oxide to ethylenediamine. The molecular weight of the propylene oxide hydrotype ranges from 500 to 7,000; and, the hydrophile, ethylene oxide, is added to constitute from 10% by weight to 80% by weight of the molecule.

2. Condensation products of one mole of alkyl phenol wherein the alkyl chain, of straight chain or branched chain configuration, or of single or dual alkyl constituent, contains from 8 to 18 carbon atoms with from 3 to 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from 6 to 24 carbon atoms with from 3 to 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co. and Alfonic® manufactured by Vista Chemical Co.

4. Condensation products of one mole of saturated or unsaturated, straight or branched chain carboxylic acid having from 8 to 18 carbon atoms with from 6 to 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol® manufactured by Henkel Corporation and Lipopeg® manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility. In a preferred embodiment the surfactant is a sorbitan ester.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from 1,000 to 3,100 with the central hydrophile including 10% by weight to 80% by weight of the final molecule. These reverse Pluronics® are manufactured by BASF Corporation under the trade name Pluronic® R surfactants.

Likewise, the Tetronic® R surfactants are produced by BASF Corporation by the sequential addition of ethylene oxide and propylene oxide to ethylenediamine. The hydrophobic portion of the molecule weighs from 2,100 to 6,700 with the central hydrophile including 10% by weight to 80% by weight of the final molecule.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

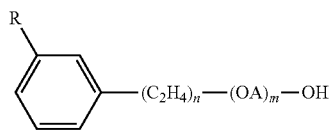

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from 1 to 6 carbon atoms and one reactive hydrogen atom, n has an average value of at least 6.4, as determined by hydroxyl number and m has a value such that the oxyethylene portion constitutes 10% to 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n(C_2H_4O)_mH]_x$ wherein Y is the residue of an organic compound having from 2 to 6 carbon atoms and containing x reactive hydrogen atoms in which x has a value of at least 2, n has a value such that the molecular weight of the polyoxypropylene hydrophobic base is at least 900 and m has value such that the oxyethylene content of the molecule is from 10% to 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from 8 to 18 carbon atoms and containing x reactive hydrogen atoms in which x has a value of 1 or 2, n has a value such that the molecular weight of the polyoxyethylene portion is at least 44 and m has a value such that the oxypropylene content of the molecule is from 10% to 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R^2CONR^1Z$ in which: $R^1$ is H, $C_1$-$C_4$ hydrocarbyl, 2-hydroxy ethyl, 2-hydroxy propyl, ethoxy, propoxy group, or a mixture thereof; R is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from 0 to 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_{10}$-$C_{18}$ ethoxylated fatty alcohols with a degree of ethoxylation of from 3 to 50.

11. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from 6 to 30 carbon atoms and a polysaccharide, e.g., a polyglycoside, hydrophilic group containing from 1.3 to 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use in the present compositions include those having the formula: $R^6CON(R^7)_2$ in which $R^6$ is an alkyl group containing from 7 to 21 carbon atoms and each $R^7$ is independently hydrogen, $C_1$-$C_4$ alkyl, $C_1$-$C_4$ hydroxyalkyl, or —$(C_2H_4O)_xH$, where x is in the range of from 1 to 3.

13. A useful class of non-ionic surfactants includes the class defined as alkoxylated amines or, most particularly, alcohol alkoxylated/aminated/alkoxylated surfactants. These non-ionic surfactants may be at least in part represented by the general formulae:

$$R^{20}—(PO)_sN—(EO)_tH,$$

$$R_20—(PO)_sN—(EO)_tH(EO)_tH, \text{ and}$$

$$R^{20}—N(EO)_tH;$$

in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula:

$$R^{20}—(PO)_v—N[(EO)_wH][(EO)_zH]$$

in which $R^{20}$ is as defined above, v is 1 to 20 (e.g., 1, 2, 3, or 4 (preferably 2)), and w and z are independently 1-10, preferably 2-5.

These compounds are represented commercially by a line of products sold by Huntsman Chemicals as nonionic surfactants. A preferred chemical of this class includes Surfonic.™. PEA 25 Amine Alkoxylate.

The treatise Nonionic Surfactants, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Semi-Polar Nonionic Surfactants

The semi-polar type of nonionic surface active agents was described supra.

Anionic Surfactants

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility.

As those skilled in the art understand, anionics are excellent detersive surfactants and are therefore favored additions to heavy duty detergent compositions. Generally, however, anionics have high foam profiles which limit their use alone or at high concentration levels in cleaning systems such as CIP circuits that require strict foam control. Anionic surface active compounds are useful to impart special chemical or physical properties other than detergency within the composition. Anionics can be employed as gelling agents or as part of a gelling or thickening system. Anionics are excellent solubilizers and can be used for hydrotropic effect and cloud point control.

The majority of large volume commercial anionic surfactants can be subdivided into five major chemical classes and additional sub-groups known to those of skill in the art and described in "Surfactant Encyclopedia," Cosmetics & Toiletries, Vol. 104 (2) 71-86 (1989). The first class includes acylamino acids (and salts), such as acylgluamates, acyl peptides, sarcosinates (e.g. N-acyl sarcosinates), taurates (e.g. N-acyl taurates and fatty acid amides of methyl tauride), and the like. The second class includes carboxylic acids (and salts), such as alkanoic acids (and alkanoates), ester carboxylic acids (e.g. alkyl succinates), ether carboxylic acids, and the like. The third class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. The fifth class includes sulfuric acid esters (and salts), such as alkyl ether sulfates, alkyl sulfates, and the like.

Anionic sulfate surfactants suitable for use in the present compositions include the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside (the nonionic nonsulfated compounds being described herein).

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives.

Anionic carboxylate surfactants suitable for use in the present compositions include the alkyl ethoxy carboxylates, the alkyl polyethoxy polycarboxylate surfactants and the soaps (e.g. alkyl carboxyls). Secondary soap surfactants (e.g. alkyl carboxyl surfactants) useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary soap surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present.

Other anionic detergents suitable for use in the present compositions include olefin sulfonates, such as long chain alkene sulfonates, long chain hydroxyalkane sulfonates or mixtures of alkenesulfonates and hydroxyalkane-sulfonates.

Also included are the alkyl sulfates, alkyl poly(ethyleneoxy) ether sulfates and aromatic poly(ethyleneoxy)sulfates such as the sulfates or condensation products of ethylene oxide and nonyl phenol (usually having 1 to 6 oxyethylene groups per molecule). Resin acids and hydrogenated resin acids are also suitable, such as rosin, hydrogenated rosin, and resin acids and hydrogenated resin acids present in or derived from tallow oil.

The particular salts will be suitably selected depending upon the particular formulation and the needs therein.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Cationic Surfactants

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure RnX+Y— and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

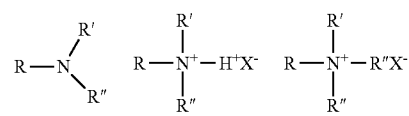

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those of skill in the art and described in "Surfactant Encyclopedia," Cosmetics & Toiletries, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1_m R^2_x YLZ$ wherein each $R^1$ is an organic group containing a straight or branched alkyl or alkenyl group optionally substituted with up to three phenyl or hydroxy groups and optionally interrupted by up to four of the following structures:

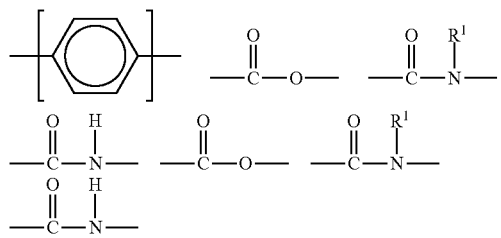

or an isomer or mixture of these structures, and which contains from 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2, or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group is filled by hydrogens.

Y can be a group including, but not limited to:

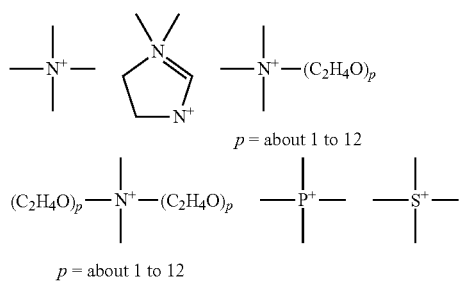

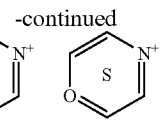

or a mixture thereof.

Preferably, L is 1 or 2, with the Y groups being separated by a moiety selected from $R^1$ and $R^2$ analogs (preferably alkylene or alkenylene) having from 1 to 22 carbon atoms and two free carbon single bonds when L is 2. Z is a water soluble anion, such as sulfate, methylsulfate, hydroxide, or nitrate anion, particularly preferred being sulfate or methyl sulfate anions, in a number to give electrical neutrality of the cationic component.

Amphoteric Surfactants

Amphoteric, or ampholytic, surfactants contain both a basic and an acidic hydrophilic group and an organic hydrophobic group. These ionic entities may be any of the anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia," Cosmetics & Toiletries, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

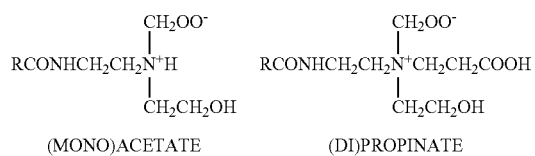

-continued

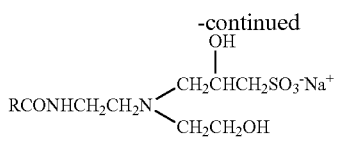

Neutral pH Zwitterion
AMPHOTERIC SULFONATE wherein R is an acyclic hydrophobic group containing from 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Preferred amphocarboxylic acids are produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reacting $RNH_2$, in which R.dbd.$C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In these, R is preferably an acyclic hydrophobic group containing from 8 to 18 carbon atoms, and M is a cation to neutralize the charge of the anion.

Preferred amphoteric surfactants include those derived from coconut products such as coconut oil or coconut fatty acid. The more preferred of these coconut derived surfactants include as part of their structure an ethylenediamine moiety, an alkanolamide moiety, an amino acid moiety, preferably glycine, or a combination thereof; and an aliphatic substituent of from 8 to 18 (preferably 12) carbon atoms. Such a surfactant can also be considered an alkyl amphodicarboxylic acid. Disodium cocoampho dipropionate is one most preferred amphoteric surfactant and is commercially available under the tradename Miranol.™ FBS from Rhodia Inc., Cranbury, N.J. Another most preferred coconut derived amphoteric surfactant with the chemical name disodium cocoampho diacetate is sold under the tradename Miranol C2M-SF Conc., also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion, a negative charged carboxyl group, and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

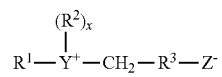

wherein R1 contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; R.sup.2 is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-car-boxylate; 5-[S-3-hydroxypropyl-S-hexadecylsulfonio]-3-hydroxypentane-1-sul-fate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propan-e-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxyl-ate; 3-[S-ethyl-S-(3-dodecoxy-2-hydroxypropyl) sulfonio]-propane-1-phosphat-e; 3-[P,P-dimethyl-P-dodecylphosphonio]-propane-1-phosphonate; and S [N,N-di (3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

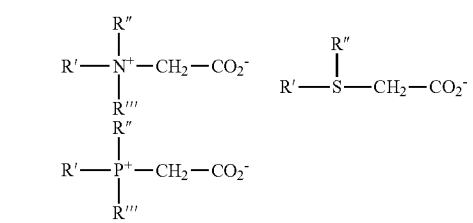

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R1)_2N.\sup.+R^2SO^3—)$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Hydrotrope

The compositions of the invention may optionally include a hydrotrope, coupling agent, or solubilizer that aides in compositional stability, and aqueous formulation. Functionally speaking, the suitable couplers which can be employed are non-toxic and retain the active ingredients in aqueous solution throughout the temperature range and concentration to which a concentrate or any use solution is exposed.

Any hydrotrope coupler may be used provided it does not react with the other components of the composition or negatively affect the performance properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, dialkyl sulfosuccinic acid esters, sugar esters (e.g., sorbitan esters), amine oxides (mono-, di-, or tri-alkyl) and $C_8$-$C_{10}$ alkyl glucosides. Preferred coupling agents for use in the present invention include n-octanesulfonate, available as NAS 8D from Ecolab Inc., n-octyl dimethylamine oxide, and the commonly available aromatic sulfonates such as the alkyl benzene sulfonates (e.g. xylene sulfonates) or naphthalene sulfonates, aryl or alkaryl phosphate esters or their alkoxylated analogues having 1 to about 40 ethylene, propylene or butylene oxide units or mixtures thereof. Other preferred hydrotropes include nonionic surfactants of $C_6$-$C_{24}$ alcohol alkoxylates (alkoxylate means ethoxylates, propoxylates, butoxylates, and co-or-terpolymer mixtures thereof) (preferably $C_6$-$C_{14}$ alcohol alkoxylates) having 1 to about 15 alkylene oxide groups (preferably about 4 to about 10 alkylene oxide groups); $C_6$-$C_{24}$ alkylphenol alkoxylates (preferably $C_8$-$C_{10}$ alkylphenol alkoxylates) having 1 to about 15 alkylene oxide groups (preferably about 4 to about 10 alkylene oxide groups); $C_6$-$C_{24}$ alkylpolyglycosides (preferably $C_6$-$C_{20}$ alkylpolyglycosides) having 1 to about 15 glycoside groups (preferably about 4 to about 10 glycoside groups); $C_6$-$C_{24}$ fatty acid ester ethoxylates, propoxylates or glycerides; and $C_4$-$C_{12}$ mono or dialkanolamides.

Chelating/Sequestering Agent

The composition may include a chelating/sequestering agent such as an aminocarboxylic acid, a condensed phosphate, a phosphonate, a polyacrylate, and the like. In general, a chelating agent is a molecule capable of coordinating (i.e., binding) the metal ions commonly found in natural water to prevent the metal ions from interfering with the action of the other detersive ingredients of a cleaning composition. The chelating/sequestering agent may also function as a threshold agent when included in an effective amount. An iminodisuccinate (available commercially from Bayer as IDS™) may be used as a chelating agent.

Useful aminocarboxylic acids include, for example, N-hydroxyethylaminodiacetic acid, ethylenediaminetetraacetic acid (EDTA), hydroxyethylenediaminetetraacetic acid, diethylenetriaminepentaacetic acid, N-hydroxyethylethylenediaminetriacetic acid (HEDTA), diethylenetriaminepentaacetic acid (DTPA), methylglycinediacetic acid (MGDA), glutamic acid-N,N-diacetic acid (GLDA), ethylenediaminesuccinic acid (EDDS), 2-hydroxyethyliminodiacetic acid (HEIDA), iminodisuccinic acid (IDS), 3-hydroxy-2-2'-iminodisuccinic acid (HIDS) and the like. The composition may also include phosphonates such as 2-phosphonobutane-1,2,4-tricarboxylic acid (PBTC), 1-hydroxyethane-1, 1-diphosphonic acid, $CH_2C(OH)[PO(OH)_2]_2$; aminotri(methylenephosphonic acid), $N[CH_2PO(OH)_2]_3$; aminotri(methylenephosphonate), sodium salt (ATMP), $N[CH_2PO(ONa)_2]_3$; 2-hydroxyethyliminobis (methylenephosphonic acid), $HOCH_2CH_2N[CH_2PO(OH)_2]_2$; diethylenetriaminepenta(methylenephosphonic acid), $(HO)_2POCH_2 N[CH_2 CH_2 N[CH_2 PO(OH)_2]_2]_2$; diethylenetriaminepenta(methylenephosphonate), sodium salt (DTPMP), $C_9 H_{(28-x)}N_3 Na_xO_{15}P_5 (x=7)$; hexamethylenediamine(tetramethylenephosphonate), potassium salt, $C_{10}H_{(28-x)}N_2K_xO_{12}P_4$ (x=6); bis(hexamethylene)triamine (pentamethylenephosphonic acid), $(HO_2)POCH_2 N[(CH_2)_2N[CH_2PO(OH)_2]_2]_2$; and phosphorus acid, $H_3PO_3$.

Thickening Agent

In some embodiments, a thickening agent may be included. Examples of thickeners include soluble organic or inorganic thickener material. Examples of organic thickening materials include, but are not limited to crosslinked homopolymers of acrylic acid, methacrylate polymers, cationic acrylate polymers, bentonite, Arabic, guar gum, xanthan gum, gellan gum, carboxymethyl cellulose, hydroxyethyl cellulose, hydroxymethyl cellulose, carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose, agar, pectin, gelatin, starch, chitosan, hydroxyethyl chitosan, polyvinyl alcohol, and polyethylene oxide polymers with a molecular weight range between about 80,000 and 10,000,000 g/mol. Examples of suitable polyethylene oxide polymers are available from DOW Chemical under the POLYOX Tradename. Some examples of inorganic thickeners include clays, silicates and other well-known inorganic thickeners. Some examples of organic thickeners include thixotropic and non-thixotropic thickeners. In some embodiments, the thickeners have some substantial proportion of water solubility to promote easy removability. Examples of useful soluble organic thickeners for the compositions of the invention comprise carboxylated vinyl polymers such as polyacrylic acids and alkali metal salts thereof, and other similar aqueous thickeners that have some substantial proportion of water solubility. The composition of a thickening agent can be present in the range of approximately 0-5% by weight; more preferably 0-3% by weight in cleaning solutions at use concentrations.

Film Forming Agent

The antimicrobial compositions of the invention can include a film forming agent. The film forming agent includes an effective amount of one or more alcohol ethoxylate compounds. Typically, one or more alcohol ethoxylate compounds include an alkyl group that has 12 or fewer carbon atoms. In at least some embodiments, alcohol ethoxylate compounds may each independently have structure represented by Formula I: R—O—(CH$_2$CH$_2$O)$_n$—H (I) wherein R is a (C$_1$-C$_{12}$) alkyl group and n is an integer in the range of 1 to 100. In some embodiments, R may be a (C$_8$-C$_{12}$) alkyl group, or may be a (C$_8$-C$_{10}$) alkyl group. Similarly, in some embodiments, n is an integer in the range of 10-50, or in the range of 15-30, or in the range of 20-25. In some embodiments, the one or more alcohol ethoxylate compounds are straight chain hydrophobes. One example of such an alcohol ethoxylate mixture is commercially available from Sasol under the trade name NOVEL II 1012-21. Alcohol ethoxylate surfactants are also described in U.S. application Ser. No. 10/703,042, assigned to Ecolab, herein incorporated by reference.

The film forming agent can comprise a very broad range of weight percent of the entire composition, depending upon the desired properties. For example, for concentrated embodiments, the sheeting agent can comprise in the range of 0.011 to about 10% wt. more preferably 0.01 to 5% by weight of the composition.

Humectant

The composition can also optionally include one or more humectants. A humectant is a substance that promotes moisture retention.

Exemplary humectants that can be used include, but are not limited to glycerin, propylene glycol, sorbitol, glucose glutame, panethol, polyethylene glycol, xylitol, sucrose, alkyl polyglycosides, polybetaine polysiloxanes, and mixtures thereof. In some embodiments, the composition can include humectant in an amount in the range of 0.05-10% by weight

Emollients

Emollients incorporated into compositions of the present invention can serve to assist in forming a protective coating on the skin to retain moisture. To be useful in the present invention, an emollient should have a soothing action on skin, should be compatible with aqueous buffered solutions of anionic surfactants, and should not significantly detract from the antimicrobial action of the components utilized in this invention. Example emollients include, but are not limited tolanolin, mineral oil, glycerine lecithin, fatty esters, substituted fatty esters, sorbitol, xylitol, methyl gluceth-21, allantoin, isohexadecane, dioctyl adipate, siloxanes, substituted siloxanes and polysiloxanes. The amount of the emollient in a composition suitable for use, should be in the range of from about 0.1% by weight to about 10% by weight.

Additional Antimicrobial Agent

The compositions may optionally include an additional antimicrobial agent or preservative. Antimicrobial agents are chemical compositions that can be used in the compositions to prevent microbial contamination and deterioration of commercial products material systems, surfaces, etc. Generally, these materials fall in specific classes including phenolics, halogen compounds, quaternary ammonium compounds, metal derivatives, amines, alkanol amines, nitro derivatives, analides, organosulfur and sulfur-nitrogen compounds and miscellaneous compounds. The given antimicrobial agent depending on chemical composition and concentration may simply limit further proliferation of numbers of the microbe or may destroy all or a substantial proportion of the microbial population. The terms "microbes" and "microorganisms" typically refer primarily to bacteria and fungus microorganisms. In use, the antimicrobial agents are formed into the final product that when diluted and dispensed using an aqueous stream forms an aqueous disinfectant or sanitizer composition that can be contacted with a variety of surfaces resulting in prevention of growth or the killing of a substantial proportion of the microbial population. Common antimicrobial agents that may be used include phenolic antimicrobials such as pentachlorophenol, orthophenylphenol; quaternary antimicrobial agents such as benzalconium chloride, cetylpyridiniumchloride; amines and nitro containing antimicrobial compositions such as hexahydro-1,3,5-tris(2-hydroxyethyl)-s-triazine, dithiocarbamates such as sodium dimethyldithiocarbamate, and a variety of other materials known in the art for their microbial properties. Antimicrobial agents may be encapsulated to improve stability and/or to reduce reactivity with other materials in the detergent composition. When an antimicrobial agent or preservative is incorporated into the composition, the composition of an antimicrobial agent can be present in the range of about 0.01% by weight to 5% by weight.

Enzymes

The composition of the invention may include one or more enzymes, which may act by degrading or altering one or more types of soil residues encountered thus removing the soil or making the soil more removable by a surfactant or other component of the cleaning composition. For example, one or more proteases can cleave complex, macromolecular protein structures present in soil residues into simpler short chain molecules which are, of themselves, more readily solubilized or otherwise more easily removed by solutions containing said proteases.

Suitable enzymes may include a protease, an amylase, a lipase, a gluconase, a cellulase, a peroxidase, or a mixture thereof of any suitable origin, such as vegetable, animal, bacterial, fungal or yeast origin. Selections are influenced by factors such as pH-activity and/or stability optima, thermostability, and stability to active detergents, builders and the like. In this respect bacterial or fungal enzymes may be preferred, such as bacterial amylases and proteases, and fungal cellulases. Preferably the enzyme may be a protease, a lipase, an amylase, or a combination thereof. Enzyme may be present in the composition from at least 0.01 wt %, or 0.01 to 2 wt %.

Enzyme Stabilizing System

The composition of the invention may include an enzyme stabilizing system. The enzyme stabilizing system can include a boric acid salt, such as an alkali metal borate or amine (e. g. an alkanolamine) borate, or an alkali metal borate, or potassium borate. The enzyme stabilizing system can also include other ingredients to stabilize certain enzymes or to enhance or maintain the effect of the boric acid salt.

For example, the cleaning composition of the invention can include a water soluble source of calcium and/or magnesium ions. Calcium ions are generally more effective than magnesium ions and are preferred herein if only one type of cation is being used. Cleaning and/or stabilized enzyme cleaning compositions, especially liquids, may include 1 to 30, 2 to 20, or 8 to 12 millimoles of calcium ion per liter of finished composition, though variation is possible depending on factors including the multiplicity, type and levels of enzymes incorporated. Water-soluble calcium or magnesium salts may be employed, including for example calcium chloride, calcium hydroxide, calcium formate, calcium malate, calcium maleate, calcium hydroxide and calcium acetate; more generally, calcium sulfate or magnesium salts corresponding to the listed calcium salts may be used. Further increased levels of calcium and/or magnesium may of course be useful, for example for promoting the grease-cutting action of certain types of surfactant.

Use Compositions

The compositions of the present invention include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired antimicrobial activity. The concentrates may be diluted with the water of dilution at a weight ratio of at least 1:2 and up to 1:256.

In other embodiments, the antiviral compositions may be combined with water to form a use solution. The use solution can include between about 0.05% to about 35% by weight of a C1 to C6 alcohol; from about 0.0002% to about 1.75% by weight of one or more alkyl 2-hydroxycarboxylic acids; from about 0.0002% to about 1.75% by weight of a sulfonated surfactant and water.

Methods Employing the Antiviral Compositions

The invention includes a method for reducing a viral population on the surface of an object, a method for reducing the population of a microorganism on skin, a method for treating a disease of skin, and the like. These methods can operate on an article, surface, in a body or stream of water or a gas, or the like, by contacting the article, surface, body, or stream with a composition of the invention. Contacting can include any of numerous methods for applying a composition of the invention, such as spraying the compositions, immersing the article in the compositions, foam or gel treating the article with the composition, or a combination thereof.

The compositions of the invention can be used for a variety of domestic or industrial applications, e.g., to reduce viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The compositions can be employed as a foaming or nonfoaming environmental sanitizer or disinfectant.

The compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compounds can be employed in an antimicrobial foot bath for livestock or people. The compositions of the present invention can also be employed as an antimicrobial teat dip.

In some aspects, the compositions of the present invention can be employed for reducing the population of pathogenic microorganisms, such as pathogens of humans, animals, and the like. The compositions exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like, most particularly non enveloped viruses. Such pathogens can cause a variety of diseases and disorders, including mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The compositions need only be applied to the skin, other external or mucosal surfaces of an animal water, air, or surface.

In some aspects, the compositions of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the compound of the invention can be employed include a milk line dairy, a continuous brewing system, food processing lines such as pumpable food systems and beverage lines, etc. Food service wares can be disinfected with the compound of the invention. For example, the compounds can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions can also be used on or in other industrial equipment and in other industrial process streams such as heaters, cooling towers, boilers, retort waters, rinse waters, aseptic packaging wash waters, and the like. The compounds can be used to treat microbes and odors in recreational waters such as in pools, spas, recreational flumes and water slides, fountains, and the like.

A filter containing the compound can reduce the population of microorganisms in air and liquids. Such a filter can remove water and air-born pathogens such as *Legionella*.

The compounds of the present invention can also be employed by dipping food processing equipment into the use solution, soaking the equipment for a time sufficient to sanitize the equipment, and wiping or draining excess solution off the equipment, The compound may be further employed by spraying or wiping food processing surfaces with the use solution, keeping the surfaces wet for a time sufficient to sanitize the surfaces, and removing excess solution by wiping, draining vertically, vacuuming, etc.

The compounds of the present invention may also be used in a method of sanitizing hard surfaces such as institutional type equipment, utensils, dishes, health care equipment or tools, and other hard surfaces.

The antiviral compounds can be applied to microbes or to soiled or cleaned surfaces using a variety of methods. These methods can operate on an object, surface, in a body or stream of water or a gas, or the like, by contacting the object, surface, body, or stream with a compound of the invention. Contacting can include any of numerous methods for applying a compound, such as spraying the compound, immersing the object in the compound, foam or gel treating the object with the compound, or a combination thereof.

A concentrate or use concentration of a compound of the present invention can be applied to or brought into contact with an object by any conventional method or apparatus for applying an antimicrobial or cleaning compound to an object. For example, the object can be wiped with, sprayed with, foamed on, and/or immersed in the compound, or a use solution made from the compound. The compound can be sprayed, foamed, or wiped onto a surface; the compound can be caused to flow over the surface, or the surface can be dipped into the compound. Contacting can be manual or by machine. Food processing surfaces, food products, food processing or transport waters, and the like can be treated with liquid, foam, gel, aerosol, gas, wax, solid, or powdered stabilized compounds according to the invention, or solutions containing these compounds.

The present invention will now be further illustrated by way of the following non-limiting examples, in which parts and percentages are by weight unless otherwise indicated.

EXAMPLES

Compositions according to the invention were prepared and tested using a standard plaque Assay Protocol per below with murine Norovirus (MNV-1).

Plaque Assay Protocol

1. Pass cells according to Tissue Culture Protocols.
2. Use hemocytometer to count cells and adjust suspension to $1 \times 10^6$ cells/ml.
3. "Prepare cell culture plates by adding 2 ml of the cell suspension to each well in a six well plate. Rock plates gently to evenly distribute cells and incubate overnight.
4. Perform the suspension assay. Ensure each dilution tube contains 1.8 ml media.
5. Prepare 10 fold dilutions by adding 0.2 ml test substance/virus to dilution tubes containing 1.8 ml media.
6. Aspirate media from cell culture plates (do not to let the cells over dry-only do a set of six plates at a time).
7. Inoculate the six well plates with 500 uL of diluted virus per well in duplicates according to dilutions indicated below:
8. Incubate plates for 1 hour at room temperature.
9. Prepare 1.5% low melting point agarose (SeaPlaque) overlay as follows:
   (a.) Calculate the Total Amount of overlay needed: 2 ml/well x the # of wells
   (b.) Re-melt 3% SeaPiaque. Add (Total Amount/2) ml to bottle.
   (c.) Add (Total Amount/2) ml of 2x complete MEM (see below) to bottle.
   (d.) Equilibrate 2x MEM to 37° C. and SeaPlaque agarose to 42° C. in a water bath. Immediately before overlaying cells, mix both together in one bottle.
10. At the end of incubation, aspirate off the virus. Slowly add 2 ml overlay to each well (touch the side of the well, do not pipet directly on the cells).
11. Allow the agarose to solidify (~5-10 min).
12. Incubate the plates@35° C. for 48 hours.
13. Place plates in fume hood and add 2-4 ml of 10% formaldehyde to each well. Allow the cells to fix overnight.
14. Aspirate off formaldehyde in fume hood.
15. Rinse plates and remove agarose plugs.
16. Add a 0.1% solution of Crystal Violet or Neutral Red to each well and allow to stain for at least 20 minutes.
17. Rinse plates.
18. Count plaques.

2× MEM (500 ml

1. Add 9.5 g MEM powder and 2.2 g Sodium bicarbonate to 500 ml Milli-Q water and mix well.
2. Then add: 56 ml FBS, 10 ml L-glutamine and 10 ml Pen/Strep solution.

10% Formaldehyde

1:10 with Milli-Q water or PBDW 0.1% Crystal Violet or Neutral Red Solution

1. Make stock solution with 1.0 g stain into 100 ml Milli-Q or PBDW
2. On the day of use, make 1:10 of stock and diluent Compositions for Testing Compositions according to the invention were prepared along with various controls per the tables below. Note that the Controls each only have the alkyl 2-hydroxylcarboxylic acid or the sulfonated surfactant but not both.

| Murine Norovirus | | | | | |
|---|---|---|---|---|---|
| | Control #1 | Control #2 | Control #3 | Example #1 | Example #2 |
| Ethanol | 40 | 40 | 40 | 40 | 40 |
| 2-hydroxyhexanoic acid | 2 | 0 | 0 | 1.5 | 1.5 |
| AOS | 0 | 0.5 | 0 | 0.5 | 0 |
| Dowfax C6L | 0 | 0 | 0.5 | 0 | 0.5 |
| Water | 58 | 59.5 | 59.5 | 58 | 58 |
| Total | 100 | 100 | 100 | 100 | 100 |
| Log Reduction | NDR* | NDR | — | >3.4 | >3.4 |

| | Control #2 | Control #3 | Control #4 | Control #5 | Example 4 | Example 5 |
|---|---|---|---|---|---|---|
| Ethanol | 40 | 40 | 40 | 40 | 40 | 40 |
| 2-hydroxyhexanoic acid | 0 | 0 | 1.5 | 2 | 1.5 | 1.5 |
| AOS | 0.5 | 0 | 0 | 0 | 0.5 | 0 |
| Dowfax C6L | 0 | 0.5 | 0 | 0 | 0 | 0.5 |
| Water | 59.5 | 59.5 | 58.5 | 58 | 58 | 58 |
| Total | 100 | 100 | 100 | 100 | 100 | 100 |
| Log Reduction | | | NDR | NDR | 3.35 | 3.35 |

| | Control #2 | Control #3 | Control #6 | Control #7 | Example 6 | Example 7 |
|---|---|---|---|---|---|---|
| Ethanol | 40 | 40 | 40 | 40 | 40 | 40 |
| 2-hydroxyhexanoic acid | 0 | 0 | 1.5 | 2 | 1.5 | 1.5 |
| AOS | 0.5 | 0 | 0 | 0 | 0.5 | 0 |
| Dowfax C6L | 0 | 0.5 | 0 | 0 | 0 | 0.5 |
| Water | 59.5 | 59.5 | 58.5 | 58 | 58 | 58 |
| Total | 100 | 100 | 100 | 100 | 100 | 100 |
| Log Reduction | — | — | NDR | NDR | >3.48 | >3.48 |

NDR = No Determined Reduction

| Polio Virus | | |
|---|---|---|
| | Control #8 | Example 8 |
| Ethanol | 70 | 70 |
| DI Water | 30 | 29 |
| 2-hydroxydecanoic acid | 0 | 0.5 |
| AOS | 0 | 0.5 |
| Total | 100 | 100 |
| Log Reduction | <0.5 | >4.25 |

| Antibacterial | | |
|---|---|---|
| | Example #9 | Example #10 |
| Ethanol | 40 | 40 |
| 2-hydroxydecanoic acid | 1.5 | 1.5 |
| AOS | 0.5 | 0.5 |
| Dowfax C6L | 0 | 0 |
| Water | 58 | 58 |
| Total | 100 | 100 |
| pH | 3.49 | 6.05 |

| Murine Norovirus | |
|---|---|
| | Log Reduction |
| Control #1 | 0.26 |
| Control #2 | NDR |
| Control #3 | NDR |

| Murine Norovirus | |
|---|---|
| | Log Reduction |
| Example 1 | 3.41 |
| Example 2 | 3.57 |
| Control #4 | NDR |
| Control #5 | NDR |
| Example 4 | 3.35 |
| Example 5 | 3.65 |
| Control #6 | NDR |
| Control #7 | NDR |
| Example 6 | 3.48 |
| Example 7 | 3.48 |

| Polio Virus | |
|---|---|
| | Log Reduction |
| Control #8 | <0.5 |
| Example 8 | 4.25 |

The following examples also show utility as actimicrobial or bactericidal compositions as tested in time-kill suspension testing exposure at 30 seconds.

| | Log Reduction | Log Reduction |
|---|---|---|
| Formulation | *S. aureus* ATCC 6538 | *E. coli* ATCC 11229 |

|  | Log Reduction | Log Reduction |
|---|---|---|
| Example #9 | >5 log | >5 log |
| Example #10 | >5 log | >5 log |

As can be seen, all of the examples of the invention reduced the Murine norovirus by greater than 3 logs. With only one of the alkyl 2-hydroxycarboxylic acid or the sulfonated surfactant either no virus reduction or in most cases less than one half of the virus reduction was observed showing the synergism of the two together. This test was conducted with Murine norovirus, a standard surrogate for human norovirus.

Further the low alcohol content of these formulations when tested against MNV-1 is designed to set the alcohol at a sub-lethal concentration as to not interfere or significantly contribute to the virucidal activity.

These compositions can be formulated with greater amounts of ethanol, isopropyl alcohol or other suitable solvent for material solubility and remain efficacious.

These disclosed compositions are intended for leave-on application and may be further developed with materials to increase their ability to stay on skin or tissue or hard surface. These materials are ancillary to the active virucidal system. They may be further enhanced by skin conditioning agents, humectants, emollients, film-formers, viscosity building agents, chelating agents and the like for functional or aesthetic properties.

What is claimed is:

1. An antiviral concentrate having activity against non-enveloped viruses including norovirus comprising:
    an alkyl 2-hydroxycarboxylic acid;
    at least 0.5 wt. % of a sulfonated surfactant, wherein the sulfonated surfactant is one or more of hexyldiphenyl oxide disulfonate or a $C_8$-$C_{18}$ alkyl diphenyl oxide disulfonate;
    at least 30 wt. % of a $C_1$ to $C_6$ alcohol; and
    water.

2. The concentrate of claim 1, wherein the alkyl 2-hydroxycarboxylic acid is a $C_6$ to $C_{20}$ alkyl 2-hydroxycarboxylic acid.

3. The concentrate of claim 1, wherein the alkyl 2-hydroxycarboxylic acid is one or more of 2-hydroxyhexanoic acid, 2-hydroxyoctanoic acid, or 2-hydroxydecanoic acid.

4. The concentrate of claim 1, wherein the $C_1$ to $C_6$ alcohol is ethanol, isopropanol, n-propanol, or a mixture thereof.

5. The concentrate of claim 4, wherein the $C_1$ to $C_6$ alcohol is ethanol.

6. The concentrate of claim 1, wherein the alkyl 2-hydroxycarboxylic acid is present in the concentrate in an amount of from about 0.5 weight percent to about 10 weight percent.

7. The concentrate of claim 1, wherein the concentrate is free of a phenolic anti-microbial.

8. The concentrate of claim 1, wherein the concentrate causes a greater than 3 log reduction in norovirus populations in less than one minute.

9. A method of reducing norovirus activity/concentration on a surface comprising:
    diluting the concentrate of claim 1 to form a use solution; and
    contacting the surface with the use solution.

10. The method of claim 9, wherein the surface is skin.

11. The method of claim 9, wherein the surface is a hard surface.

12. The method of claim 9, wherein the use solution has a pH of from about 1.5 to about 6.8.

13. The method of claim 9, wherein the concentrate is diluted with water at a weight ratio of about 1:2 to about 1:256.

14. The method of claim 9, wherein the concentrate is diluted prior to or at the point of use to form the use solution.

15. The method of claim 9, wherein the alkyl 2-hydroxycarboxylic acid is one or more of 2-hydroxyhexanoic acid, 2-hydroxyoctanoic acid, or 2-hydroxydecanoic acid.

16. The method of claim 9, wherein the $C_1$ to $C_6$ alcohol is ethanol.

\* \* \* \* \*